United States Patent
Gresl et al.

Patent Number: 5,507,755
Date of Patent: Apr. 16, 1996

[54] APPARATUS AND METHOD FOR CLOSING PUNCTURE WOUNDS

[75] Inventors: Charles Gresl, San Francisco; Albert K. Chin, Palo Alto; Tim J. Kovac, Los Gatos; Edwin J. Hlavka, Palo Alto, all of Calif.

[73] Assignee: Origin Medsystems, Inc., Menlo Park, Calif.

[21] Appl. No.: 279,513

[22] Filed: Jul. 25, 1994

Related U.S. Application Data

[63] Continuation-in-part of Ser. No. 100,926, Aug. 3, 1993, Pat. No. 5,391,182.

[51] Int. Cl.$^6$ ............................................. A61B 17/04
[52] U.S. Cl. ..................... 606/139; 606/148; 606/232
[58] Field of Search ........................... 606/139, 144–148, 606/1, 232

[56] References Cited

U.S. PATENT DOCUMENTS

| | | | |
|---|---|---|---|
| 4,493,323 | 1/1985 | Albright et al. | 128/340 |
| 4,669,473 | 6/1987 | Richards et al. | 128/334 |
| 4,744,364 | 5/1988 | Kensey | 128/334 |
| 5,021,059 | 6/1991 | Kensey et al. | 606/213 |
| 5,053,046 | 10/1991 | Janese | 606/215 |
| 5,061,274 | 10/1991 | Kensey | 606/213 |
| 5,085,661 | 2/1992 | Moss | 606/139 |
| 5,171,259 | 12/1992 | Inoue | 606/213 |
| 5,192,300 | 3/1993 | Fowler | 606/213 |
| 5,222,508 | 6/1993 | Contarini | 128/898 |
| 5,257,637 | 11/1993 | El Gazayerli | 128/898 |
| 5,281,234 | 1/1994 | Wilk | 606/139 |
| 5,282,827 | 2/1994 | Kensey | 606/215 |
| 5,304,184 | 4/1994 | Hathaway et al. | 606/148 |
| 5,368,601 | 11/1994 | Sauer et al. | 606/144 |
| 5,374,275 | 12/1994 | Bradley et al. | 606/144 |

OTHER PUBLICATIONS

Product Literature for Prior Art: "The ENDO–JUDGE Synergistic Technologies, Inc.", 1994.
Product Literature for: "FLEXIFLO T–Fastener Set", Jan. 1993.

*Primary Examiner*—Gary Jackson
*Attorney, Agent, or Firm*—Limbach & Limbach

[57] ABSTRACT

An apparatus for suturing deep puncture wounds utilizes a capturing member which is pivotally mounted to the distal end of an elongate rod. During use, the capturing member is inserted into a body cavity through a trocar sheath positioned in a wound and pivoted into a position in which it extends beneath the tissue surrounding the wound. A membrane or other suture-capturing surface is formed on the surface of the capturing member. A suture to be applied to the wound has anchors on each of its ends, and suture-carrying needles carry each of the suture ends and their corresponding anchors. The suture-carrying needles are individually passed through the tissue layers surrounding the wound and subsequently passed through the membrane of the capturing member. The suture ends and corresponding anchor means are released from the needles. The capturing means is pivoted to position in which it extends longitudinally of the elongate rod, causing the anchors to become engaged by the membrane by virtue of their inability to pass through the membrane unless carried by a needle. A lifting force is applied to the elongate rod to lift the capturing member out of the wound, pulling the ends of the suture out of the wound to close the opening in the tissue.

14 Claims, 9 Drawing Sheets

APPARATUS AND METHOD FOR CLOSING PUNCTURE WOUNDS

RELATED APPLICATIONS

This application is a Continuation-in-Part of U.S. application Ser. No. 08/100,926, filed Aug. 3, 1993, now U.S. Pat. No. 5,391,182.

FIELD OF THE INVENTION

The present invention relates to the field of surgical instruments and particularly to instruments for use in applying sutures to deep wounds.

BACKGROUND OF THE INVENTION

For laparoscopic surgery, pointed surgical instruments, called trocars, are used to provide access to body cavities by creating puncture openings through the abdominal wall. Laparoscopic surgery often requires trocar punctures measuring 10 mm in diameter or larger. These punctures can only adequately be closed using suture closure of the fascia, the thick fibrous layer of tissue which lies between the muscle and the peritoneum. If the fascia is not properly sutured, the peritoneum and bowel may begin to protrude through the fascial opening, a condition called postoperative incisional hernia.

The most common method for closing these puncture openings utilizes a curved suture needle. The skin, subcutaneous fat, and muscle are retracted away from the puncture opening and the fascia is identified. The curved needle and the attached suture are passed through the fascia on one side of the puncture opening, through the abdominal cavity, and back through the fascia on the opposite side of the puncture opening. The ends of the suture are subsequently pulled closed and tied to close the puncture opening.

While frequently successful, complications may arise from the use of this method. If the patient is obese, several inches of subcutaneous fat must be retracted away in order for the fascia to be isolated. The thick layer of fat causes the fascial tissue through which the needle is to be inserted to be recessed several inches from the exterior of the abdominal wall, making manipulation of the needle between the thick walls of fat and tissue difficult. Because the procedure involves passing the needle into the abdomen, poor control of the needle may result in puncture of the underlying bowel or inadvertent incorporation of the bowel into the fascial closure.

Two other devices have also been used for fascial closure. One, the REMA device, comprises a long member which is inserted into the puncture hole with its distal end positioned in the abdominal cavity. Once the distal end of the long member is inside the abdominal cavity, a pair of needle-carrying members are extended laterally from the distal end of the long member. The needle-carrying members hold two needles with their pointed needle tips directed towards the interior surface of the abdominal wall, such that the axes of the needles are parallel to the axis of the long member. Each needle carries one end of a single suture. The long member is then pulled outward of the puncture hole in a longitudinal direction, causing the tips of the suture-carrying needles to advance towards the skin surface of the abdominal wall. A needle-clamping device is advanced towards the suture-carrying needles, engages with the needles and removes them from the abdominal wall. The suture ends are removed from the needles and tied off, the needles are retracted by the needle-carrying member, and the apparatus is removed from the abdominal cavity via the puncture hole.

The suture tie applied by the REMA device passes through the entire abdominal wall, including the skin, fat, and muscle. Necrosis of the skin and muscle tissue may occur because of the strongly tensioned suture tie that is required to close the strong and fibrous fascial layer. Moreover, because the REMA needles pass outwardly through the skin from the abdominal cavity, the device exposes the surgeon to the risk of being injured by the blind passage of sharp needles through the abdominal wall.

Another method involves inserting a suture through fascial tissue using a needle, retrieving the suture from the needle inside the abdominal cavity using a grasper, withdrawing the needle and reinserting it at a second location, passing the suture from the grasper to the needle inside the abdominal cavity, and withdrawing the needle with the suture attached. While this method satisfactorily sutures the opening, transfer of the suture between the needle and the grasper requires visualization inside the abdominal cavity, and thereby requires an additional trocar opening for insertion of a laparoscope. An additional closure method is thus needed for closing the trocar puncture used for the laparoscope.

OBJECTS AND SUMMARY OF THE INVENTION

It is an object of the present invention to provide an apparatus and method for performing suture closure of wounds and other puncture openings in tissue.

The apparatus and method of the present invention provide a technique for threading the ends of a suture into the body through the tissue surrounding a puncture opening or wound, for capturing the suture ends inside the body, and for looping the ends out of the body through the wound so as to create a suture loop which, upon tightening, reapposes the tissue. Other devices for retrieving the ends of a suture inside a body and for looping the ends through the wound and out of the body are shown and described in U.S. application Ser. No. 08/100,926 which is incorporated herein by reference. Inventions of this type are especially suitable for closing deep wounds and puncture openings that penetrate the fascial layer.

The invention utilizes a capturing member pivotally attached to the end of an elongate member and which is inserted through a trocar sheath positioned in the wound and into the body cavity underlying the wound. Once inside the body cavity, the capturing member is pivoted into a position in which it extends laterally from the elongate member, where it receives the ends of a suture passed through the tissue surrounding the wound. Once it has received the suture ends, the capturing member is withdrawn out of the wound, carrying the ends of the suture out of the wound to tighten the suture and close the opening in the tissue.

DETAILED DESCRIPTION OF THE PREFERRED EMBODIMENTS

By way of introduction, it should be explained that the preferred suturing device according to the present invention (shown in FIGS. 1 through 9I) comprises a single elongate member which, during the course of its use, is folded at one (FIG. 9A) or all (FIG. 1) of three V-shaped live hinges 70, 78, 82. Fabricating the device from a single elongate member allowing pivoting movement of sections via the live hinges reduces material cost and simplifies manufacturing. Of course, it is intended that the device can alternatively be constructed by assembling independent sections which combine to form the functional equivalent of the preferred illustrative embodiment shown.

Figure 9A:
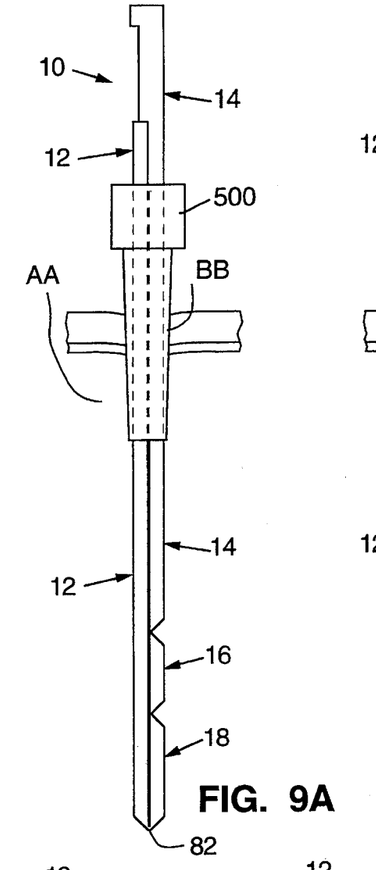
FIGS. 9A–9I are a sequence of from elevational views showing the use of the preferred suturing device according to the present invention.

For the purposes of this description, the terms "proximal" and "distal" will be used to refer to relative positions of the various features of the device as they exist when the device is folded at hinge point 82 as shown in FIG. 9A.

Referring to FIGS. 1–6C, the preferred suturing device 10 is comprised generally of a spine 12, a push rod 14, a suture-capturing member 16 joined in hinged relationship to the push rod 14, and a hinge member 18 joined in hinged relation to the suture-capturing member 16 at one end and to the spine 12 at the other end. The push rod 14 is longitudinally slidable relative to the spine 12 between a first position (see FIG. 9A) in which the suture-capturing member 16 and the hinge member 18 extend substantially longitudinally of the push rod 14, and a second position (shown in FIG. 1) in which the suture-capturing member 16 extends angularly of the push rod 14 and the hinge member 18 extends angularly between the suture-capturing member 16 and a distal portion of the spine 12. When in the second position, the suture-capturing member 16 may extend from the push rod 14 at a 90° angle as shown in the drawings, or at an angle other than 90°.

Figure 8:
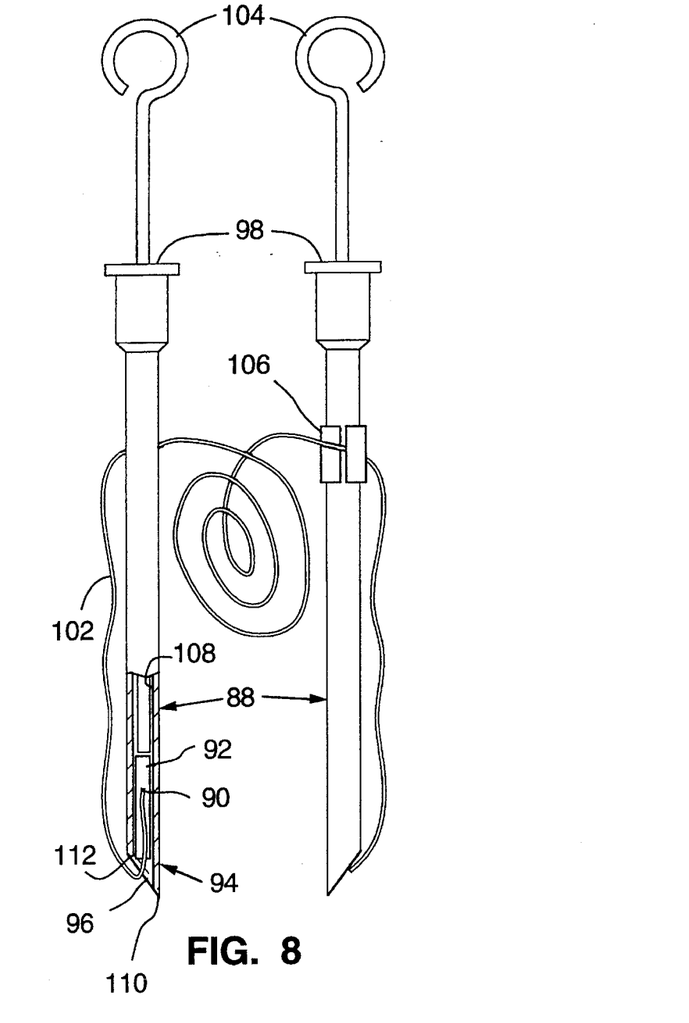
FIG. 8 is a partial cross-sectional side view of a pair of needles of the type shown in FIG. 7A.

Operation of the apparatus of present invention will be described in detail below. Briefly stated, implementation of the preferred suture device 10 involves inserting the suture-capturing member 16 and the hinge member 18 through a wound in a patient's body when the push rod 14 is in its first position, and subsequently advancing the push rod 14 distally to pivot the suture-capturing member 16 into the second position. The ends of a suture are each individually carried by one of a pair of suture-carrying needles 88 (FIG. 8). The needles, with the suture ends attached to them, are advanced through tissue surrounding the wound and subsequently through the suture-capturing member 16 (FIGS. 9D and 9G). The suture ends are released from the needles and the needles are withdrawn, leaving the suture ends threaded through the tissue and the suture-capturing member 16 (FIG. 9E). The push rod 14 is next advanced proximally to move the suture-capturing member to the first position (FIG. 9H), and the suture device 10 is withdrawn from the wound, carrying the suture ends and anchors out of the wound to tighten the suture (FIG. 9I).

Figures 2A, 2B:
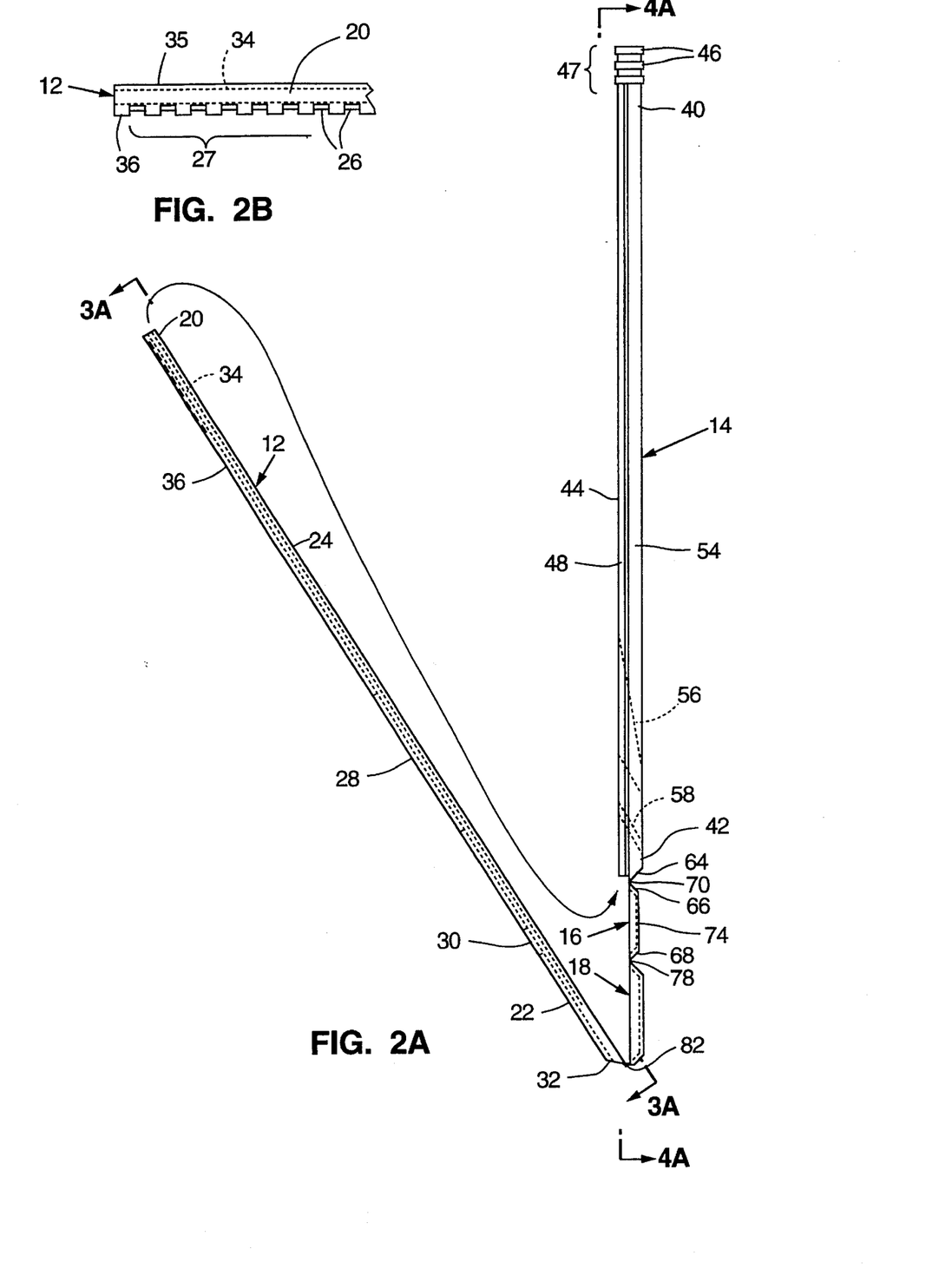
FIG. 2A is a front elevational view of the suturing device of FIG. 1, showing for simplicity the spine and the push rod disassembled from each other.
FIG. 2B is an enlarged front elevational view of the proximal portion of the spine of the suturing device of FIG. 1.
Figure 3A:
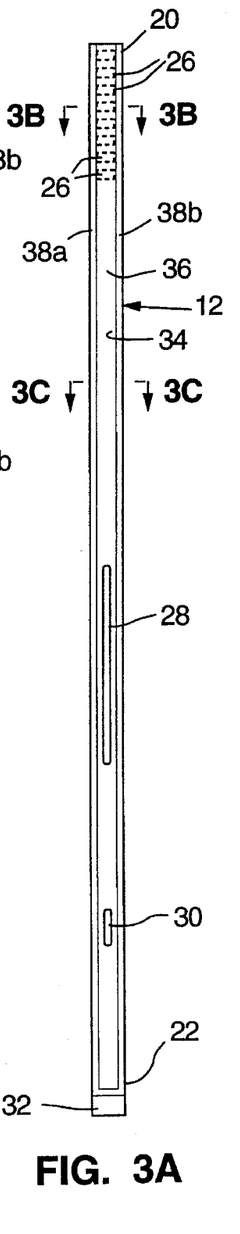
FIG. 3A is a side elevational view of the spine of the suturing device of FIG. 1.

Referring to FIGS. 2A and 3A, the spine 12 is an elongate rod having a proximal portion 20, a distal portion 22, and an intermediate portion 24 between the proximal and distal portions. The distal portion 22 of the spine 12 preferably has a tapered end 32.

Figure 3B:
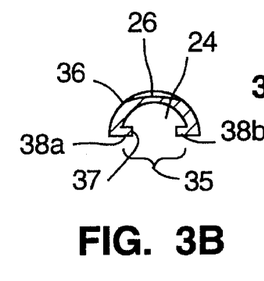
FIGS. 3B and 3C are cross-sectional top views of the spine taken along the planes designated 3B—3B and 3C—3C in FIG. 3A.
Figure 3C:
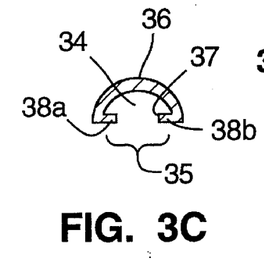

As shown in FIGS. 3B and 3C, the spine 12 preferably has a semi-circular cross-section defined by an arcuate wall 36 on one side and a pair of flat, inwardly-extending shoulders 38a, 38b on the other side. Together, the shoulders 38a, 38b form flat side 35 of the spine 12. The shoulders 38a, 38b and the arcuate wall 36 extend longitudinally along the spine 12 as shown in FIG. 3A.

An elongate channel 34 is formed along flat side 35 of the spine 12. The channel 34 has a reduced-width portion 37 formed between the shoulders 38a, 38b.

A plurality of spaced recesses 26 are formed in arcuate wall 36 at the proximal portion 20 of the spine 12 as shown in FIG. 2B. The recesses 26, which are substantially perpendicular to the longitudinal axis of the spine 12, form a textured gripping surface 27 which helps the user to maintain a solid grip on the spine 12 during use. It should be noted that, although recesses 26 are illustrated, gripping surface 27 could be formed with any texture suitable for secure operation.

A pair of elongate through-slots 28, 30 (FIG. 3A) are formed in the intermediate portion 24 of the spine 12. The through-slot 28 is preferably substantially longer than the through-slot 30 for reasons more fully described below.

Figure 4A:
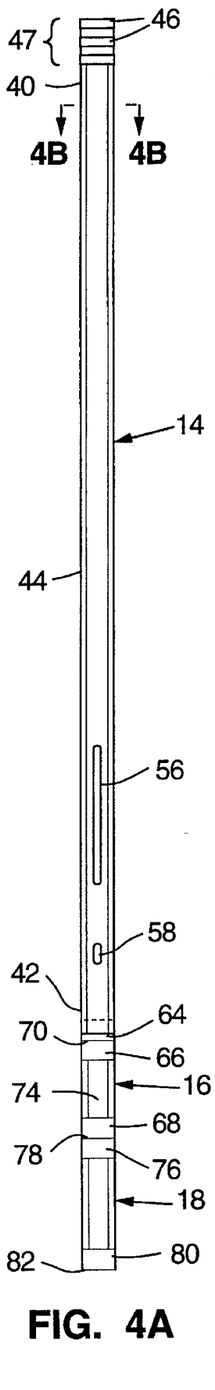
FIG. 4A is a side elevational view of the push rod of the suturing device of FIG. 1.
Figure 4B:
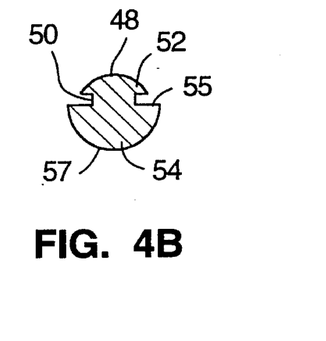
FIG. 4B is a cross-sectional top view of the push rod taken along the plane designated 4B—4B in FIG. 4A.

Referring to FIGS. 2A and 4A, the push rod 14 is elongate and has a proximal portion 40, a distal portion 42, and an intermediate portion 44 between the proximal and distal portions. A plurality of spaced ribs 46 are formed at the proximal portion 40 of the push rod 14. The spaced ribs 46 provide a suitable gripping surface 47 which facilitates handling of the push rod 14 by a user.

The push rod 14 is formed with two elongate sections, each of which extends longitudinally between the proximal and distal portions 40, 42. The first elongate section is base member 54 defined by a flat side 55 and an arcuate side 57. The second elongate section is rib 48. Rib 48 has a neck 50 extending from the flat side 55 and a head 52 which is broader than the neck 50.

Figure 1:
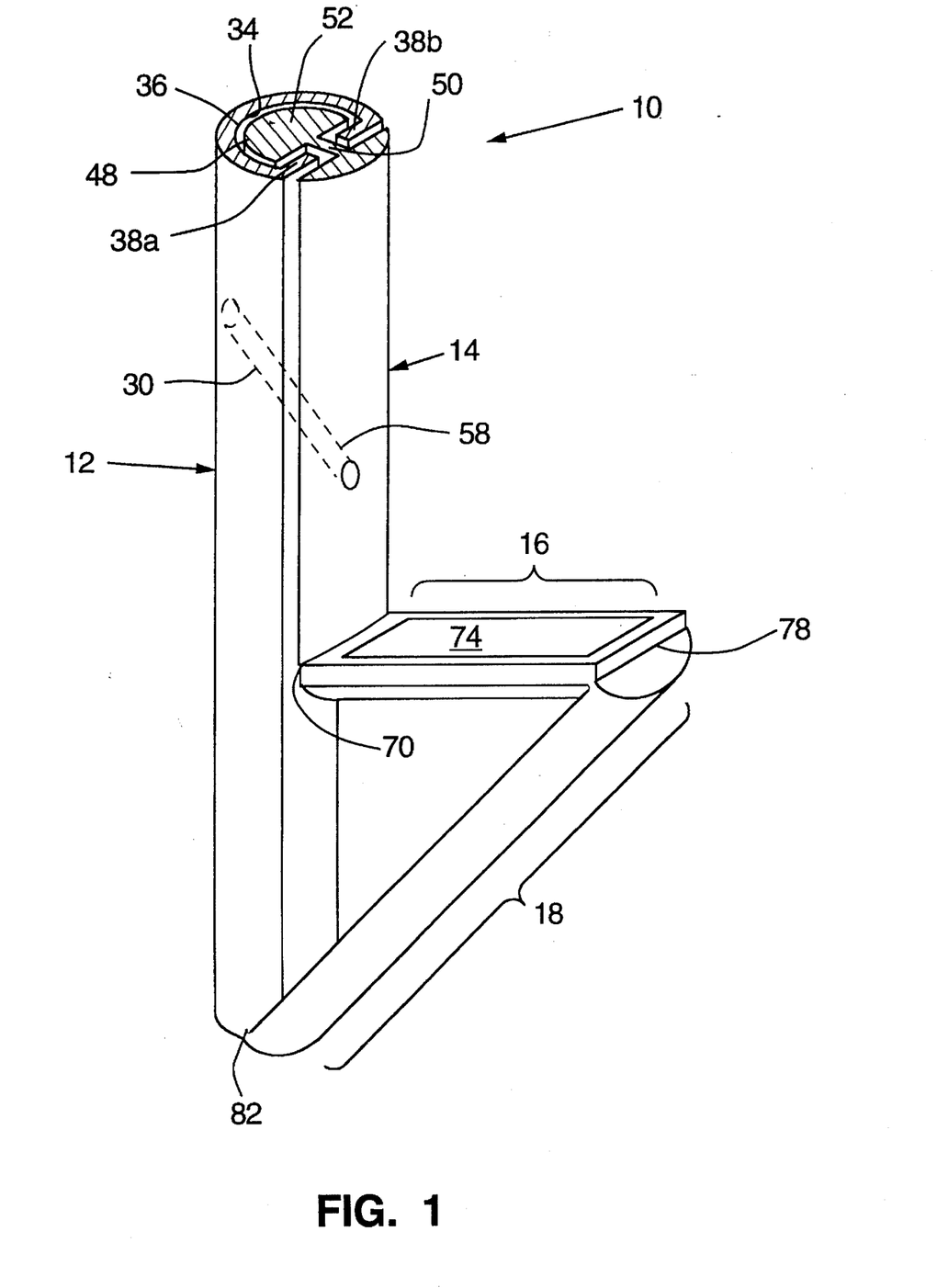
FIG. 1 is a perspective view of a first suturing device according to the present invention, showing the spine and the push rod in partial cross-section.

As can be seen in FIG. 1, when the device is fully assembled, the rib 48 is slidable within the channel 34 with the neck 50 passing between the shoulders 38a, 38b of the spine 12. The shoulders 38a, 38b are configured to prevent the head 52 from leaving the channel 34 and thereby prevent the spine 12 and push rod 14 from separating when engaged in this manner. This is important during operation because external pressure, which might otherwise cause the spine 12 and push rod 14 to separate, may be exerted downwardly against the suture-capturing member 16 when it is penetrated by a suture needle. Thus, the device is configured to prevent such an undesirable result when in the assembled, operational condition shown in FIG. 1.

Intermediate portion 44 of the push rod 14 has a pair of angled through-slots 56, 58. Referring to the longitudinal cross-sectional view of the push rod 14 shown in FIG. 5A, the through-slot 56 preferably has a broad end 60 and a narrow end 62. The broad end 60 originates at the rib 48 and tapers towards the narrow end 62 which is located at the base section 54 of the push rod 14. The through-slot 56 is positioned such that when the push rod 14 is in the second position (the position shown in FIG. 1), the broad end 60 is aligned with the through-slot 28 (FIG. 3A) in the spine 12. Similarly, the through-slot 58 on the push rod 14 is positioned to align with the through-slot 30 (FIG. 3A) in the spine 12 when the push rod 14 is in the second position.

The through-slots 56, 58 are oriented such that when the push rod 14 is in the second position, a needle (such as the needle 88 shown in FIGS. 7A and 8) may be introduced into either of the through-slots 28, 30 in the spine, subsequently passed through the corresponding one of the through-slots 56, 58 in the push rod 14, and inserted through the suture-capturing member 16.

It is contemplated that the invention could employ a plurality of through-slots having various angles or flares to provide differing needle approaches and selective needle positioning control as are suited for the particular application. For example, in the alternative embodiment of the push rod 14a shown in FIG. 5B, a flared through-slot 56a is provided which allows the needle to be positioned in one of a number of different angles when it is passed through the through-slot 56a.

Distal portion 42 of the push rod 14 has a tapered end 64, which is connected to the suture-capturing member 16. The suture-capturing member 16 has a tapered proximal end 66 (which is attached to the tapered end 64 of the push rod 14) and a tapered distal end 68. The suture-capturing member 16 and the push rod 14 are joined such that the tapered ends 64, 66 form a V-shaped live hinge 70 between them. It is preferred that tapered, or rounded, ends be used throughout the device to minimize external sharp surfaces which could cause trauma to adjacent tissue.

Figures 5A, 5B, 6A, 6B, 6C:
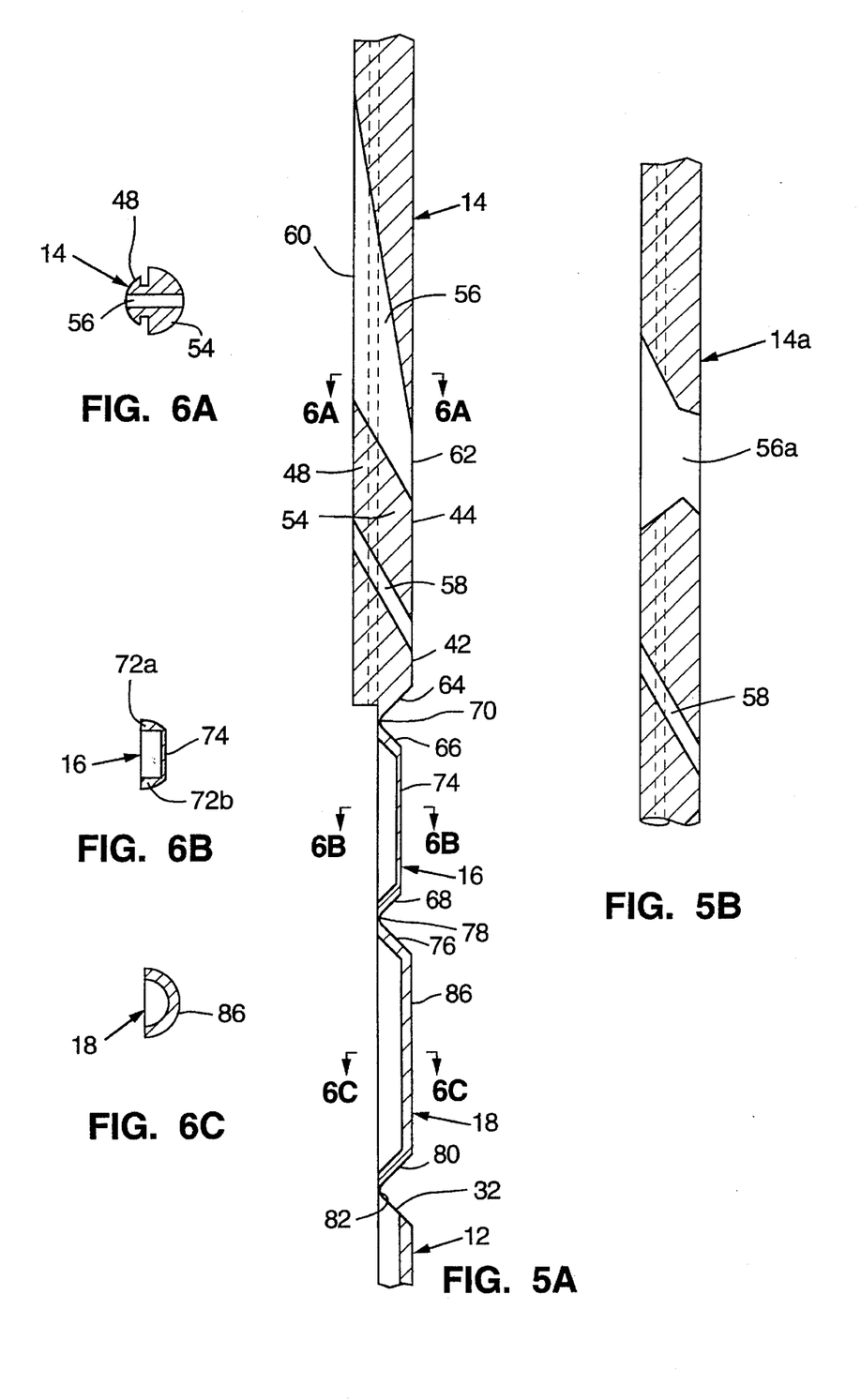
FIG. 5A is cross-sectional front view of the push rod of FIG. 4A.
FIG. 5B is a cross-sectional front view of an alternative embodiment of the push rod of FIG. 4A.
FIGS. 6A, 6B, and 6C are cross-sectional top views of the push rod taken along the planes designated 6A—6A, 6B—6B, and 6C—6C in FIG. 5A.

Referring to the cross-section view of the suture-capturing member 16 shown in FIG. 6B, the suture-capturing member 16 has a pair of side walls 72a, 72b and a capturing surface 74 extending between the side walls 72a, 72b. The capturing surface 74 is formed of a material that may be penetrated by a suture-carrying needle 88 (see FIG. 7A). Capturing surface 74 may be made integral with member 16 or as a separate, connected component. In the preferred embodiment, the capturing surface 74 is preferably formed of polypropylene having a thickness that is sufficiently small to allow the passage of a suture-carrying needle through it. Capturing surface 74 may alternatively be formed of elastic polymers, suitable plastics, metal foil, elastomeric materials, various inelastic membranes, mesh, woven fabric, screen, or other punctuate material removeably or permanently secured to member 16. Alternatively, capturing surface 74 may be slotted integral material of member 16 to allow passage of a suture-carrying needle through one of a plurality of slots or apertures.

Connected to the distal end 68 of the suture-capturing member 16 is hinge member 18. Hinge member 18 has a tapered proximal end 76 which is joined to distal end 68 of the suture-capturing member 16 to form a V-shaped live hinge 78. Of course, these hinged connections could be formed by other conventional mechanical hinge means other than live hinge constructions.

The hinge member 18 also has a tapered distal end 80 which is joined to the tapered proximal end 32 of the spine 12 to form a third V-shaped live hinge 82. Referring to FIG. 6C, the hinge member 18 has a semi-circular cross-section defined by a wall 86. The wall 86 is preferably of sufficient thickness to block the passage of a suture-carrying needle so as to prevent inadvertent puncture of tissue underlying the hinge member 18 during use. Thus, hinge member 18 functions as a needle guard or stop to prevent undesired suture advancement.

The suture device 10 is preferably formed of molded polypropylene and is preferably formed in a single piece. Alternatively, the spine 12, push rod 14, suture-capturing member 16 and hinge member 18 may be separate pieces which are joined together at their respective ends using one of a number of types of hinging devices.

Figure 7A:
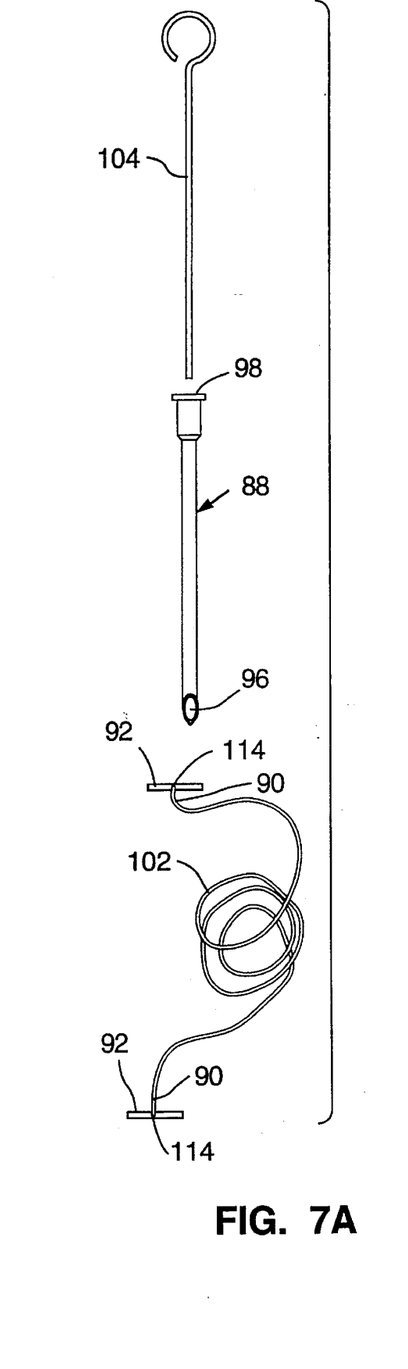
FIG. 7A is a side elevational view of a suture, suture needle, and plunger of the present invention.
Figure 7B:
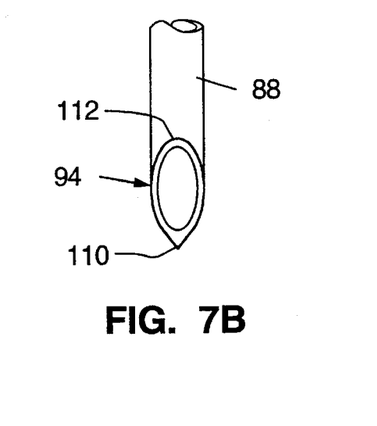
FIG. 7B is a side elevational view of the needle tip of FIG. 7A.

Referring to FIGS. 7A through 8, the present invention preferably utilizes a pair of hollow needles 88. The needles 88 carry anchors 92 that are attached to each end 90 of a suture 102. Each needle 88 has a throughbore 108 (FIG. 8) and is open at its proximal and distal ends 98, 96, respectively. Each of the anchors 92 is carried in the throughbore 108 of one of the needles, close to the distal end 96 of the needle 88 as shown in FIG. 8. Plungers 104, which may be in the form of stylets, are positioned in the needle throughbores 108 at the proximal ends 98 of the needles 88. When the plungers 104 are manually depressed, they travel longitudinally in the needle throughbores 108 in a distal direction, forcing the anchors 92 out of the needle throughbores 108 through the distal ends 96.

The portions of the suture which are adjacent to the anchors 92 extend longitudinally along the exterior surface of the needles and tuck into split sleeves 106 formed near the proximal ends 98 of the needles. The split sleeves 106 hold the suture 102 in place but are capable of releasing the suture 102 when a tensile force is applied to the suture, such as when an anchor 92 is ejected from needle throughbore 108 by plunger 104.

As shown in FIG. 8, the distal ends 96 of the needles 88 are beveled to form a sharp point 110 and a dull short side 112. The short side 112 is dulled to prevent the suture 102 from being accidentally cut by the sharp point 110.

The preferred anchors 92 for use with the present invention are shown in FIG. 7A. The anchors 92 are tubes that are preferably formed from stainless steel. Alternatively, anchors 92 could be formed of plastic, or formed as a plastic or metal bead, a glue ball, a woven know or other suitable structure. In the preferred steel embodiment, each anchor 92 has a hole 114 midway of its length. An end of the suture 102 is positioned in each hole 114 and the tube is crimped down around it to form a swaged connection. When allowed to hang freely from the suture 102, the anchors 92 assume a substantially horizontal state.

Use of the preferred embodiment will next be described with reference to FIGS. 9A to 9I. The suture device 10 is initially placed in the first position shown in FIG. 9A such that the suture-capturing member 16 and hinge member 18 extend substantially longitudinally of the push rod 14 and such that these components are substantially adjacent to the spine 12. A trocar sheath 500 is positioned in a wound opening BB and the suture device 10 is passed through the trocar sheath 500 to position the suture-capturing member 16 and the hinge member 18 in a body cavity AA beneath the wound opening, as shown in FIG. 9A.

Figures 9B, 9C:
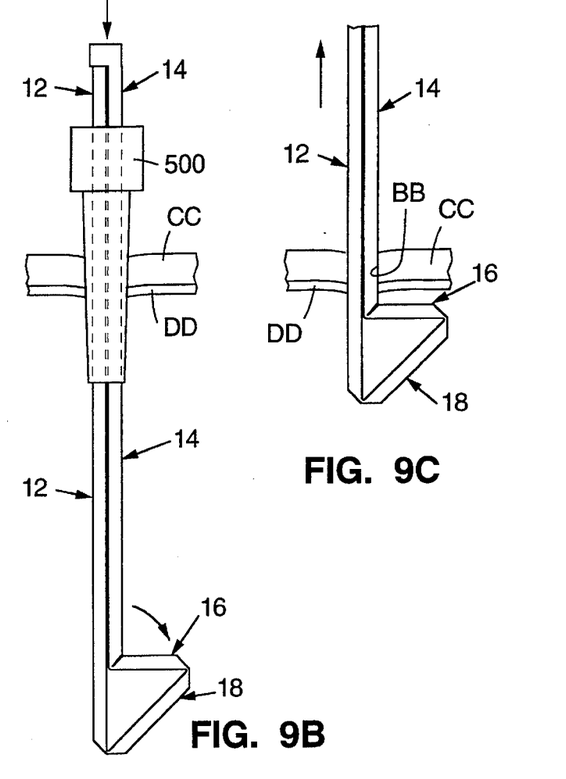
Figures 9D, 9E, 9F:
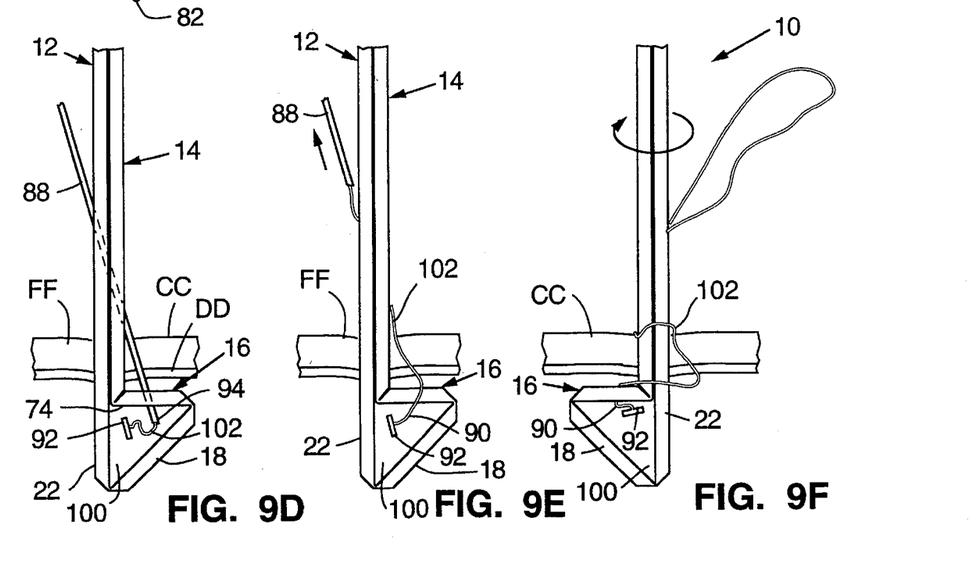
Figures 9G, 9H, 9I:
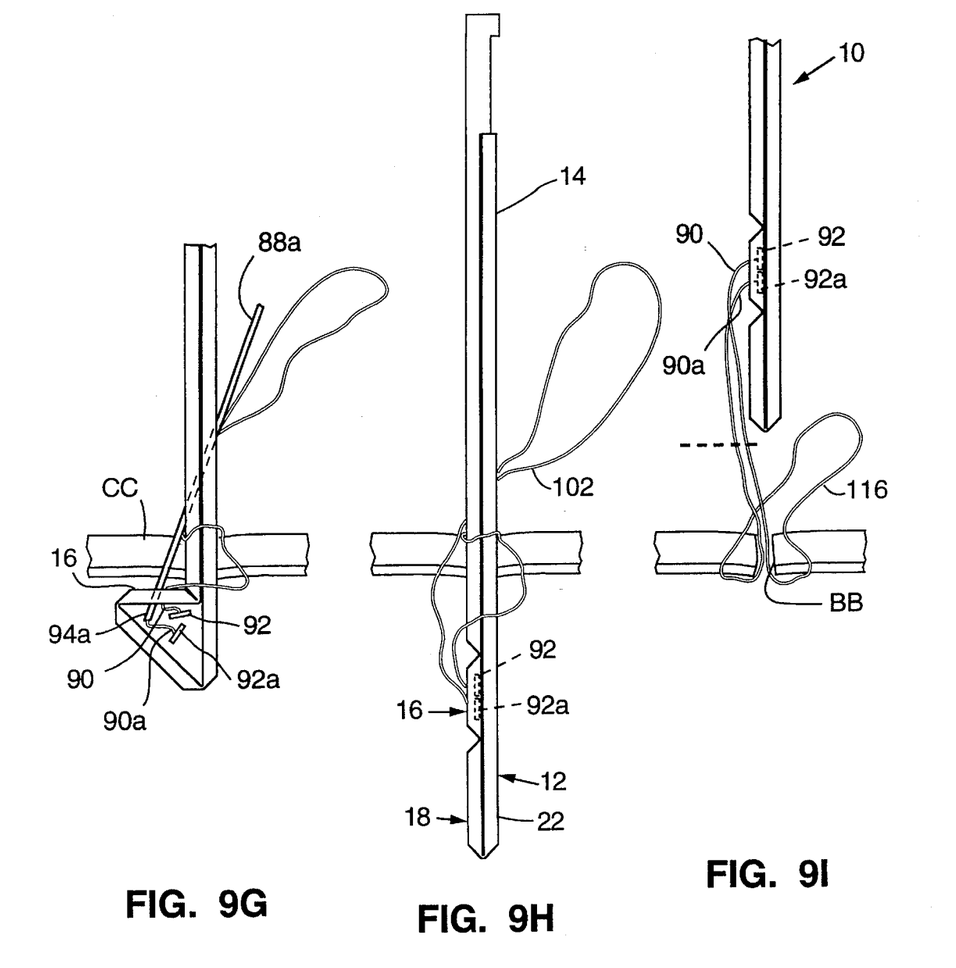

Next, the push rod 14 is advanced distally to cause the suture-capturing member 16 and the hinge member 18 to pivot away from the spine 12 and into the second position, as shown in FIG. 9B. The trocar sheath 500 is next removed from the wound BB and the suture device 10 is moved in a proximal direction, as indicated by the arrow in FIG. 9C, to position the suture-capturing member 16 beneath tissue CC (including the fascial layer DD) adjacent to the wound opening BB.

Next, a suture-carrying needle 88 carrying a suture 102 and an anchor 92 attached to the suture (as described above with reference to FIGS. 7A and 8) is inserted through the through-slots 28, 56 (not shown in FIGS. 9C and 9D) in the spine 12 and push rod 14, respectively. The needle 88 may alternatively be inserted through the through-slots 30, 58 (also not shown), if necessary to achieve a desired needle insertion angle. The needle tip 94 is next passed through the tissue CC, which may include (or be limited to, if upper layer FF of tissue is retracted away) the fascial layer DD. The needle 88 may also be inserted directly through the tissue CC, i.e. without first passing through through-slots in the spine 12 and push rod 14.

The needle tip 94 is subsequently passed through the capturing surface 74 of suture-capturing member 16, to position the needle tip 94 within a triangular region 100 bounded by the suture-capturing member 16, the hinge member 18, and the spine 12 (FIG. 9D). The hinge member 18 prevents unwanted needle advancement by acting as a stop to protect bowel or other tissue. The anchor 92 is released from the needle tip 94 by the plunger 104 in the manner described with respect to FIGS. 7A and 8, and the needle 88 is withdrawn as shown in FIG. 9E, leaving the suture end 90 and the anchor 92 within the triangular region 100.

The suture device 10 is next rotated through an angle of approximately 180° to position the suture-capturing member 16 beneath a different portion of the tissue CC. As shown in FIG. 9G, a second needle 88a carrying a second anchor 92a attached to a second end 90a of the suture 102 is passed through the through-slots, through the tissue CC and through the suture-capturing member 16. Once the needle tip 94a is positioned within the triangular region 100, the anchor 92a and suture end 90a are released from the needle 88a and the needle is withdrawn.

Next, as shown in FIG. 9H, the push rod 14 is withdrawn in a proximal direction, causing the suture-capturing member 16 and the hinge member 18 to fold into the first position, thereby capturing the anchors 92, 92a between the suture-capturing member 16 and the spine 12. It may be necessary to tension the suture before withdrawing the push rod 14, so as to ensure that the anchors 92, 92a are captured by the suture-capturing member 16.

As shown in FIG. 9I, the suturing device 10 is next withdrawn from the wound BB carrying with it the suture ends 90, 90a and anchors 92, 92a and thereby fondling a suture loop 116 through the tissue. The suture loop 116 is tightened by the application of a tensile force on the suture ends 90, 90a and the suture is subsequently tied and cut.

Figures 10, 11, 12A, 12B, 13A, 13B:
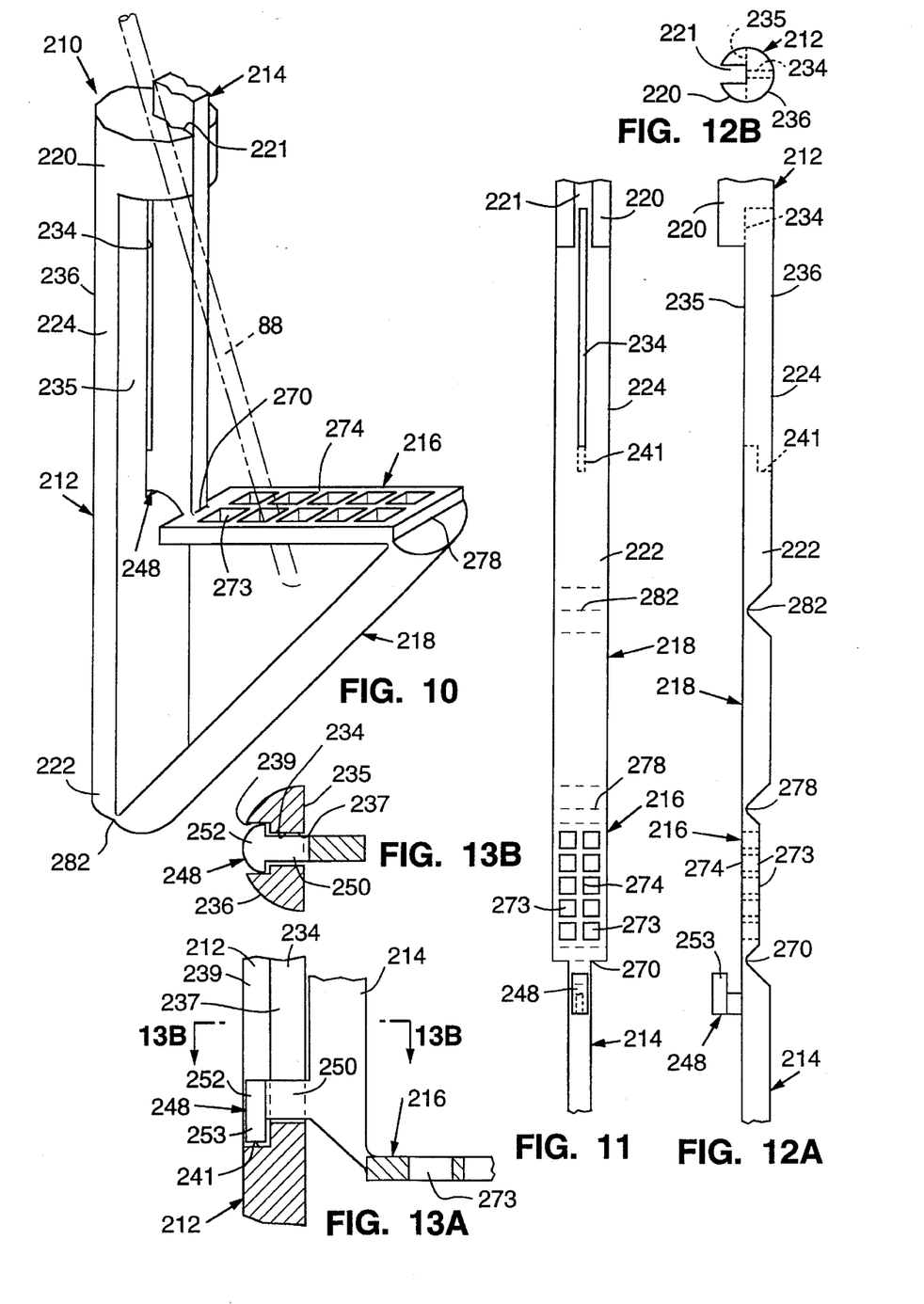
FIG. 10 is a partial perspective view of a second embodiment of a suturing device according to the present invention.
FIG. 11 is a partial side elevational view of the suturing device of FIG. 10.
FIG. 12A is a partial from elevational view of the suturing device of FIG. 10.
FIG. 12B is a partial top elevational view of the spine of the suturing device of FIG. 10.
FIG. 13A is a cross-sectional side view showing a portion of the spine, push rod, and suture-capturing member of the suturing device of FIG. 10.
FIG. 13B is a cross-sectional top view showing the spine and the push rod of the suturing device of FIG. 10.

FIG. 10 shows a first alternative embodiment of a suturing device 210 according to the present invention. Suturing device 210 is comprised of a spine 212, a push rod 214, a suture-capturing member 216 joined in hinged relation to the push rod 214, and a hinge member 218 joined in hinged relation to the suture-capturing member 216 at one end and to the spine 212 at the other end. As with the first embodiment, the spine 212, push rod 214, suture-capturing member 16, and hinge member 218 are joined in hinged relation at hinge points 270, 278 and 282.

The push rod 214 is longitudinally slidable relative to the spine 212 between first and second positions. In the first position, (equivalent to the first position of the preferred suture device 10, see FIG. 9A) the suture-capturing member 216 and the hinge member 218 extend substantially longitudinally of the push rod 214. In the second position (shown in FIG. 10) the suture-capturing member 216 extends laterally of the push rod 214 and the hinge member 218 extends angularly between the suture-capturing member 216 and a distal portion of the spine 212.

The spine 212 has a proximal portion 220, a distal portion 222, and an intermediate portion 224 between the proximal and distal portions 220, 222. As shown in FIGS. 10 and 12B, proximal portion 220 has a substantially circular cross-section and a slot 221 extending through it in a longitudinal direction.

The intermediate portion 224 of the spine has a substantially semi-circular cross-section defined by a flat side 235 and an arcuate side 236 (see FIG. 13B). An elongate channel 234 (FIGS. 11 and 13B) is formed in the intermediate portion 224 of the spine 212 and extends from the flat side 235 to the arcuate side 236. As can be seen in the cross-section view of FIG. 13B, the channel 234 has a reduced width portion 237 near the flat side 235 of the spine 212 and a broad portion 239 near the arcuate side 236.

The channel 234 extends longitudinally through the intermediate portion 224 of the spine 212. As shown in FIGS. 11, 12A and 13A, the broad portion 239 of the channel 234 is slightly longer than the reduced width portion 237 such that it forms a distally-extending pocket 241.

As shown in FIG. 10, the push rod 214 is an elongate member, a portion of which is slidably disposed within the slot 221 in the proximal portion 220 of the spine 212. Extending from the push rod 214 is a catch member 248 (FIGS. 12A, 13A, 13B) having a neck portion 250 and a head portion 252. A tab 253 extends from head portion 252 in a distal direction.

The catch member 248 is slidably disposed within the channel 234, with its neck portion 250 slidably disposed within reduced width portion 237 of channel 234 and with its head portion 252 disposed within broad portion 239 of the channel 234, as shown in FIG. 13B.

When the push rod 214 is moved between the first and second positions, the catch member 248 slides longitudinally within the channel 234. As shown in FIG. 13A, the distally-extending tab 253 of the catch member 248 sits within the pocket 241 when the push rod 214 is in the second position. In this manner, spine 212 and push rod 214 are prevented from separating in response to the application of force against the suture-carrying member 216, such as when a needle 88 is being passed through it as shown with respect to the first embodiment in FIG. 9D.

The suture-capturing member 216 of the second embodiment is comprised of a grid 274 of spaced holes 273. The holes 273 are sized to allow passage of a suture-carrying needle 88 (see FIG. 7A and the accompanying description), with suture ends 90 and anchors 92 attached. They are also sized to inhibit passage of anchors 92 (not shown in FIGS. 10–13B) which have been released from the suture-carrying needle 88.

Figures 14, 15:
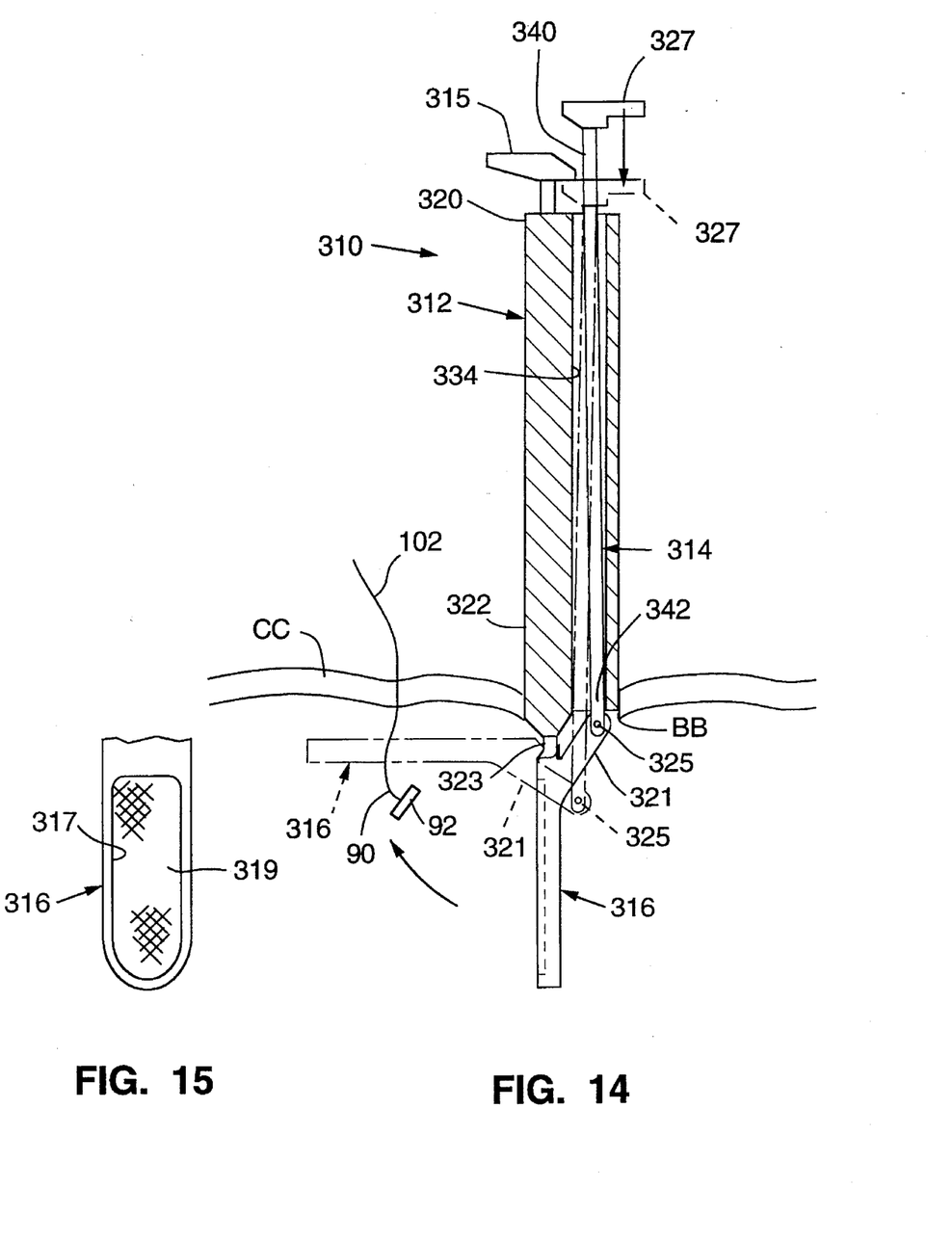
FIG. 14 is a cross-sectional from view of a third embodiment of a suturing device according to the present invention, showing in broken lines the suture-capturing member in its second position.
FIG. 15 is a top elevational view of the suture-capturing member of the suturing device of FIG. 14.

A third embodiment of a suturing device 310 is shown in FIGS. 14 and 15. The suturing device 310 of the third embodiment is comprised of a spine 312 having a proximal portion 320 and a distal portion 322. A throughbore 334 extends longitudinally through the spine 320. A latch member 315 is mounted to the proximal portion 320 of the spine 312.

A first hinge 323 is mounted to the distal portion 322 of the spine 312. A suture-capturing member 316 is mounted to the hinge for pivotal movement relative to the distal portion 322 of the spine 312. As illustrated in FIG. 14, the suture-capturing member 316 has a cut-out portion 317 which is covered by a suture-capturing surface 319 (preferably formed of a fabric, mesh, or inelastic membrane).

A pivot member 321 extends from the suture-capturing member 316, towards distal portion 322 of the spine 312.

A push rod 314 is slidably disposed within the throughbore 334 in the spine 312. The push rod 314 has a distal end 342 pivotally mounted to the pivot member 321 by a pivot pin 325. The push rod 314 also has a proximal end 340, to which a second latch member 327 is mounted.

As with the first and second embodiments, the suture device 310 of the third embodiment is moveable between first and second positions. In the first position, shown in solid lines in FIG. 14, the suture-capturing member 316 extends substantially longitudinally of the spine 316. In the second position, shown in broken lines in FIG. 14, the suture-capturing member 316 extends laterally of the spine 312, beneath tissue CC through which a suture 102 is to be extended. Movement between the first and second positions is effected by sliding the push rod 314 within the throughbore 334 of the spine 312, as indicated by the arrow in FIG. 14, thereby pivoting the suture-capturing member 316 about the hinge 323 and the pivot point 325.

To apply a suture 102 using the suture device 310 of the third embodiment, the suture-capturing member 316 is moved into the first position, inserted through the wound opening BB, and then pivoted into the second position by advancing the push rod 314 distally within the throughbore 334. The suture-capturing member 316 is next locked in the second position by engaging the locking members 315,327 with each other.

A needle 88 (FIG. 8) carrying the end 90 of a suture 102 and an anchor 92 attached to the end 90 is passed through tissue CC surrounding the wound and through the suture-carrying membrane 319.

Next, the spine 312 is rotated approximately 180° (not shown) to re-position the suture-capturing member 316 beneath a second region of the tissue CC, and a second suture end is passed through the tissue and the suture-capturing member 316 as described with respect to the first embodiment. The suture-capturing member 316 is returned to the first position and is removed from the wound, carrying the suture ends 90 and anchors 92 with it.

Conclusion

While three embodiments of the present invention have been described, many others are possible according to the present invention. For example, the preferred embodiment as well as alternative embodiments could be modified to provide a single needle which could carry multiple anchors. Thus, a single needle would be used with two or more passes, each pass deploying an anchor. The requirement of two needles would then be eliminated and the device would benefit from a more simple construction. The multiple anchors would be loaded into the single needle and suitable plunger mechanisms (detents, etc.) inside the needle would be used to deploy the anchors individually and sequentially. The scope of the present invention is not intended to be limited to the specific embodiment described above; it should be defined by the claims recited below.

We claim:

1. A suturing device for use in retrieving from a body cavity the ends of a suture passed through tissue surrounding a wound and inserted into the body cavity by a needle having a tip, the suturing device comprising:

a first elongate member having a proximal portion and a distal portion;

a capturing member coupled to the distal portion of the first elongate member, the capturing member pivotable between a first position wherein the capturing member extends substantially longitudinally of the first elongate member, and a second position wherein the capturing member extends laterally of the first elongate member;

suture capturing means on the capturing member, for capturing a suture passed through the tissue and into the body cavity;

a suture having anchoring means thereon, the anchoring means for passage through the tissue by the needle, and for anchoring the suture to the capturing means while within the body cavity; and actuator means for pivoting the capturing member from the first to the second position after the capturing member has been inserted through the wound into the body cavity, and from the second to the first position after the suture has been captured by the capturing surface.

2. The suturing device of claim 1 wherein:

the capturing means comprises a capturing surface secured to the capturing member, the capturing surface having properties which allow passage therethrough of the needle carrying a suture and anchoring means, but which inhibit passage therethrough of the suture and anchoring means after they have been released from the needle tip.

3. The suturing device of claim 2 wherein the capturing member is comprised of a frame having an open portion, and the capturing surface comprises a membrane covering the open portion.

4. The suturing device of claim 2 wherein the capturing member is comprised of a frame having an open portion, and the capturing surface comprises a mesh fabric covering the open portion.

5. The suturing device of claim 2 wherein the capturing member and capturing surface are comprised of a frame having a plurality of slots.

6. The suturing device of claim 2, further comprising a needle guide connected to the elongate member, the needle guide sized for receiving the needle and oriented to guide the needle for passage through the capturing surface.

7. The suturing device of claim 1 wherein:

the apparatus further comprises a second elongate member having a distal end; and the actuating means comprises a hinge member connected in hinged relation to the capturing member and further connected in hinged relation to the distal end of the second elongate member, the second elongate member being longitudinally slidable between a first position, wherein the capturing member extends substantially longitudinally of the first elongate member, and a second position wherein the second elongate member is positioned distal to its first position and wherein the capturing member is pivoted into its second position.

8. A suturing device for use in passing a suture having ends through tissue surrounding a wound and into a body cavity beneath the wound, and for retrieving the ends of the suture from the body cavity through the wound, the suturing device comprising:

a suture;

needle means for carrying the suture through tissue surrounding the wound and into the body cavity;

a first elongate member having a proximal portion and a distal portion;

a capturing member coupled to the distal portion of the first elongate member, the capturing member pivotable between a first position wherein the capturing member extends substantially longitudinally of the first elongate member, and a second position wherein the capturing member extends angularly of the first elongate member;

suture capturing means on the capturing member, for capturing the suture after it has been carried through the tissue and into the body cavity by the needle means;

anchoring means on the suture, for passage through the tissue by the needle means, and for anchoring the suture to the capturing means while within the body cavity; and actuator means for pivoting the capturing member from the first to the second position after the capturing member has been inserted through the wound into the body cavity, and from the second to the first position after the suture has been captured by the capturing surface.

9. The suturing device of claim 8 wherein:

the needle means is further for releasing the suture and anchoring means from the needle means inside the body cavity;

the capturing means comprises a capturing surface formed on the capturing member, the capturing surface having properties which allow passage therethrough of the needle means carrying a suture and anchoring means, but which inhibit passage therethrough of the suture end and anchoring means after they have been released from the needle means.

10. The suturing device of claim 8 wherein:

the apparatus further comprises a second elongate member having a distal end; and the actuating means comprises a hinge member connected in hinged relation to the capturing member and further connected in hinged relation to the distal end of the second elongate member, the second elongate member being longitudinally slidable between a first position, wherein the capturing member extends substantially longitudinally of the first elongate member, and a second position wherein the second elongate member is positioned distal to its first position and wherein the capturing member is pivoted into its second position.

11. A method of closing a wound with a suture, comprising the steps of:

(a) providing an elongate member, a capturing member joined in hinged relationship to the elongate member, an actuator for moving the capturing member between a first position in which it extends substantially longitudinally of the elongate member and a second position in which it extends angularly of the elongate member, a suture having a least two ends, and anchors connected to each end of the suture,;

(b) positioning the capturing member in the first position;

(c) after step (b), inserting the capturing member through the wound and into a body cavity underlying the wound;

(d) after step (c), moving the capturing member into the second position using the actuator;

(e) passing the suture ends with the suture anchors thereon through tissue surrounding the wound and into the underlying body cavity;

(f) engaging the suture anchors, with the suture ends attached, with the capturing surface of the capturing member;

(g) after step (f), moving the capturing member into the second position; and (h) after step (g), withdrawing the capturing member, with the suture ends and anchors engaged with it, out of the body cavity and out of the wound.

12. The method of claim 11 wherein:

the providing step further provides (1) a capturing surface on the capturing member, the capturing surface formed such that a needle tip carrying suture ends and anchors can pass through it, and such that after release of the suture ends and anchors from the needle tip, the anchors cannot easily pass through the capturing surface, and (2) a needle having a needle tip;

the passing and engaging steps includes the steps of:

attaching the suture ends with the suture anchors thereon to the needle tip, passing the needle tip through the tissue surrounding the wound and into the underlying body cavity, passing the needle tip through the capturing surface, and releasing the suture ends with the suture anchors from the needle tip.

13. A method of using a suture capturing device, comprising the steps of:

(a) providing an elongate member, a capturing member joined in hinged relationship to the elongate member, and an actuator for moving the capturing member between a first position in which it extends substantially longitudinally of the elongate member and a second position in which it extends angularly of the elongate member;

(b) positioning the capturing member in the first position;

(c) after step (b), inserting the capturing member through a trocar sleeve;

(d) moving the capturing member into the second position using the actuator; and (e) removing the capturing member through the trocar sleeve.

14. A suturing device for use in retrieving from a body cavity end regions of a suture having anchors on its end regions after the end regions and sutures are passed through tissue surrounding a wound and inserted into the body cavity, the suturing device comprising:

an elongate member; and a capturing member extending laterally of the first elongate member, the capturing member including a suture capturing portion configured to capture anchors attached to a suture following insertion of the suture through the tissue and into the body cavity.

* * * * *